United States Patent [19]

Farr et al.

[11] Patent Number: 5,382,709
[45] Date of Patent: Jan. 17, 1995

[54] ALPHA-MANNOSIDASE AND FUCOSIDASE INHIBITORS

[75] Inventors: Robert A. Farr, Loveland; Norton P. Peet, Cincinnati, both of Ohio

[73] Assignee: Merrell Dow Pharmaceuticals Inc., Cincinnati, Ohio

[21] Appl. No.: 75,984

[22] Filed: Jun. 11, 1993

Related U.S. Application Data

[60] Division of Ser. No. 666,742, Mar. 13, 1991, Pat. No. 5,240,707, which is a continuation-in-part of Ser. No. 508,875, Apr. 12, 1990, abandoned.

[51] Int. Cl.⁶ .................. C07C 205/00; C07C 35/06
[52] U.S. Cl. ................................ 568/704; 568/838
[58] Field of Search .............. 514/23; 424/405, 85.1, 424/85.7, 94.61, 408, 409, 410, 422, 423; 568/704, 838

[56] References Cited

PUBLICATIONS

White et al, Biochem. & Biophys. Research Communications, 150(2):615–625, (1988).
McDowell, Virology, 161:37–44 (1987).
Myc et al, Cancer Research, 49:2879–83, (Jun. 1, 1989).
Winkler et al, J. Med. Chem, 32:2084–89, (1989).
Dennis, Cancer Research, 46:5131–6, (Oct. 1986).
Farr et al, Tetrahedron Letters, 31(49):7109–7112, (1990).
Inhibition of Metastatic Potential by Fucosidase: An NMR Study Identifies a Cell Surface Metastasis Marker, Wright et al, Journal of Cellular Biochemistry 37:49–59 (1988).
Increased Serum α-L-Fucosidase and β-N-Acetyglucosaminidase Activities in Diabetic, Cirrhotic and Gastric Cancer Patients; Reglero et al., Clinica Chmiica Acta, 103 (1980) 155–158.
Mechanism of Inhibition of Jack Bean α-Mannosidase by Swainsonine; Kang et al., Plant Physiol. (1983) 71:551–554.
Serum α-L-Fucosidase: A New Marker for the Diagnosis of Primary Hepatic Carcinoma? Deugnier, et al., Hepatology, vol. 4, No. 5, 889–892, 1984.
A Spectroscopic Investigation of Swainsonine: an α-Mannosidase Inhibitor Isolated from *Swainsona canescens*, Colegate, et al., Aust. J. Chem., 1979, 32:2257–64.
Studies of an Immunomodulator, Swainsonine, I. Hino et al., The Journal of Antibiotics, vol. XXXVII, No. 7, pp. 926–935.
Studies of an Immunomodulator, Swainsonine, II. Hino et al., The Journal of Antibiotics, vol. XXXVII, No. 7, pp. 936–940.
Biosynthesis, Meth. Enzymol. 179 (1989) p. 468.
Tetrahedron Letters, vol. 31, No. 49, pp. 7109–7112 (1990), Farr et al.
Bernet et al., Helvetica Chimica Acta 62, Fasc. 7 (1979) NR. 245, pp. 2400–2410.

*Primary Examiner*—Douglas W. Robinson
*Assistant Examiner*—Maria Luisa Osoteo
*Attorney, Agent, or Firm*—William R. Boudreaux; Stephen L. Nesbitt

[57] ABSTRACT

Substituted (1α, 2β, 3α or β,4α,5α or β)-2,3,4-trihydroxy-5-(hydroxymethyl)cyclopentylamines are inhibitors of alphamannosidase and alpha-fucosidase and are useful immunostimulants, antiviral and antimetastatic agents.

4 Claims, No Drawings

ALPHA-MANNOSIDASE AND FUCOSIDASE INHIBITORS

This is a division, of application Ser. No. 07/666,742, filed Mar. 13, 1991, now patented, Ser. No. 5/240,707 which is a continuation in part of application Ser. No 07/508,875 filed Apr. 12, 1990, now abandoned.

BACKGROUND OF THE INVENTION

Swainsonine is a substance isolated from Swainsona sp. and locoweed as well as from the fungus *Rhizoctonia leguminicola* and of the Metarhizium species. It has been reported to be a potent inhibitor of alpha-mannosidase and to block glycoprotein synthesis. Colegate et al., *Aust. J. Chem.*, 32: 2257-2264, 1979. More recently, Swainsonine was reported to counteract the immunosuppresant activity of agents such as the immunosuppressive factor obtained from tumor bearing mice, cyclophosphamide, and mitomycin C. Kino et al., *J. Antibiotics*, 38(7), 926-935, 1985. Moreover, the ability of Swainsonine to inhibit the metastatic growth of B16 melanoma cells in lungs has been reported. Kino et al., *J. Antibiotics*, 38(7),936-940, 1985. These results suggest the use of Swainsonine to improve immunresponsiveness where compromised by tumor or infection.

Alpha-mannosidase inhibitors such as Swainsonine are believed to function as immunomodulators and to reduce tumor metastatis by virtue of their ability to interfere with glycoprotein processing, a complex intracellular process in which specific sugars are clipped from a previously more complex oligosaccharide. This interference profoundly affects the resulting glycoprotein of the cell wall, and this, in turn, can affect vital receptors of target cells and of viral membrane as well as the ability of affected cells to bind to other materials. Virus-cell fusion and viral membrane formation can thus be prevented or reduced causing an antiviral effect. In a similar manner, metastasis, which depends on the ability of tumor cells to bind to other tumor cells and to other substances can be interrupted and an antimetastitic effect produced.

α-Fucosidase, a lysosomal enzyme which catabolizes glycoproteins, is increased considerably in patients with hepatic carcinoma (Deugnier, Y. et al., *Hepatology* 4: 889-892, (1984)). Increased levels of the enzyme, when measured in the serum of these patients, can provide useful diagnostic markers for the disease. Significantly higher levels of α-fucosidase activities in serum of patients with diabetes mellitus, hepatic cirrhosis and gastric carcinoma have been reported (Reglero, A. et al., *Clin. Chem. Acta* 103: 155-158, (1980)). When metastatic rat mammary adenocarcinoma cells treated with fucosidase were injected subcutaneously into rats only 20% of them showed metastases as compared to 80% of untreated cells (Wright, L. C. et al., *J. Cell Biochem.* 37: 49-59,(1988)). α-L-fucose plays a fundamental role in the process of inhibition of macrophages migration. Thus, increased activities of fucosidase in tumors can be interpreted as a possible mechanism by which cancer cells may directly subvert the process of macrophages activation, thus facilitating xenoplastic growth. Thus, inhibition of α-fucosidase may provide a useful approach to metastasis.

Applicants have now discovered a new class of alpha-mannosidase and fucosidase inhibitors which are useful as immunomodulators and as antimetastatic agents.

SUMMARY OF THE INVENTION

This invention relates to novel alpha-mannosidase and fucosidase inhibitors of formula 1

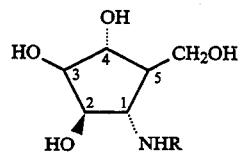

wherein R is a ($C_1$–$C_6$)alkyl optionally substituted with one or two hydroxy groups, a glycosyl group or a group of the formula —$(CH_2)_n$—Ar wherein n is an integer of from 1 to 4 and Ar is a phenyl group optionally substituted with one or two groups selected from ($C_1$–$C_4$)alkyl, ($C_1$–$C_4$)alkoxy, F, Cl, Br, I, amino, mono($C_1$–$C_4$)alkylamino, or di($C_1$–$C_4$)alkylamino, or a pharmaceutically acceptable salt thereof are alpha-mannosidase and alpha-fucosidase inhibitors and are useful in the treatment of certain vital diseases, as immunostimulants, and as antimetastitic agents.

DETAILED DESCRIPTION OF THE INVENTION

The usual stereochemical conventions are used throughout to denote the relative spatial orientation of groups attached to the rings. Thus, a solid line diverging from the point of attachment to a ring, indicates that the attached group is in the beta-configuration, that is, the group is above the plane of the ring. Likewise, a dotted line indicates that the attached group is in the alpha-configuration, that is, the group is below the plane of the ring. Attachment of a group to a ring by a normal, not divergent or dotted, line indicates that the spatial orientation can be either alpha or beta.

The ($C_1$–$C_6$)alkyl groups of this invention can be straight chained, branched chain or cyclic. Examples of such alkyl groups are methyl, ethyl, n-propyl, isopropyl, n-butyl, isobutyl, tert-butyl, n-pentyl, isopentyl, cyclopentyl, n-hexyl, and cyclohexyl.

In those alkyl groups substituted with two hydroxy groups, the hydroxy groups will not be bonded to the same carbon atom. Further, the hydroxy group will not be bonded to the carbon atom which is bonded to the amino nitrogen atom.

The glycosyl groups of this invention can be mono-, di- or trisaccharide moieties. The glycosyl group can be attached to the amino nitrogen atom through either an exocyclic or ring carbon atom of the glycosyl pentose or hexose ring thereby forming a variety of possible positional isomers for each individual glycosyl group. Also similar or dissimilar pentose or hexose moieties may be linked to each other through a glycosidic oxygen bridge wherein the bridging oxygen atom is attached to an exocyclic and/or endocyclic carbon atom of the pentose or hexose moiety of which the glycosyl radical is comprised; again all positional isomers are contemplated as within the scope of this invention.

Exemplary of glycosyl radicals contemplated are such monosaccharides as glucosyl, galactosyl, mannosyl, fucosyl, ribosyl, 2-deoxyglucosyl, 3-O-methylglucosyl, xylosyl, and arabinosyl, disaccharides as alpha- and beta-cellobiosyl, isomaltosyl, trehalosyl, and maltosyl, and such trisaccharides as maltotriosyl, and cellotriosyl. Particularly preferred are the compounds wherein R is mannosyl, glucosyl, L-fucosyl, N-acetyl-glucosyl, or cellobiosyl.

Acid addition salts with pharmaceutically acceptable acids referred to above are equivalent to the amines for the purposes of this invention. Illustrative of such salts are the salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acid. Such salts can be obtained by standard procedures from an amine of this invention and the appropriate acid.

Of those compounds of formula 1, those compounds wherein R is a methyl or ethyl, a 2,3-dihydroxypropyl, 2-hydroxypropyl, glucosyl and mannosyl are preferred. Also preferred are those compounds of formula 1 wherein the hydroxymethyl group is in the beta-configuration. Further preferred are those compounds wherein the substituent at the 3 position is beta and the substituent at the 5 position is beta and wherein the substituent at the 3 position is alpha and the substituent at the 5 position is alpha.

The compounds of formula 1 (3β-configuration) are prepared by protecting group removal from the compounds of formula 2

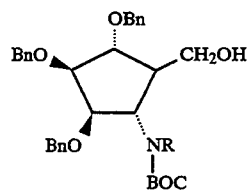

2 wherein R is as defined above. When R is an alkyl group, preferably the ring hydroxy groups are protected with benzyl groups (Bn) which can be removed in the usual manner such as by catalytic hydrogenation. Subsequently the amino group will be protected with a tert-butyloxycarbonyl group (BOC) which can be removed in the usual manner such as by mild acid hydrolysis conditions.

The compounds of formula 2 wherein the hydroxymethyl group is in the α-configuration, i.e. the compounds of formula 2a,

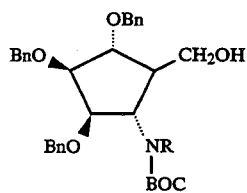

2a are prepared by the reduction of a 3H-cyclopent[c]isoxazole of formula 3

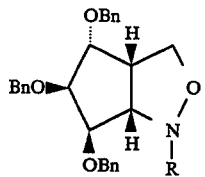

3 wherein R is a ($C_1$–$C_6$)alkyl group. The reduction can be accomplished by any means known to those skilled in the art for reduction of the oxygen-nitrogen bond provided that the reaction conditions do not substantially affect the relative stereochemistry of the groups. For example, a formula 3 compound can be reacted with an excess (2-5 molar) of activated zinc dust and an acid such as acetic acid. Typically this reaction is performed at a temperature of from about room temperature to about the reflux temperature of the mixture. The acid itself is usually the solvent and preferably will be an aqueous acetic acid solution such as an 85% aqueous acetic acid solution. The reaction will be substantially complete in from about one-half hour to about 2 or 3 hours after which time the secondary amino product, after isolation using standard techniques, is treated with tert-butyloxycarbonyl anhydride (($Boc$)$_2$O) to give the desired formula 2a compound.

The compounds of formula 2 wherein the hydroxymethyl group is in the β-configuration, i.e. the compounds of formula 2b,

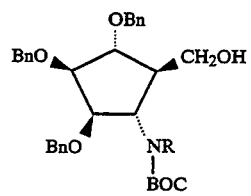

2b are prepared by isomerization of the formula 2a compound. This can be accomplished in any manner which does not substantially affect the stereochemistry at the other positions. For example, the appropriate compound of formula 2a can be subjected to careful oxidation such as by treatment with the Dess-Martin periodinane. The resulting aldehyde of formula 4a

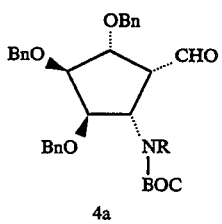
4a

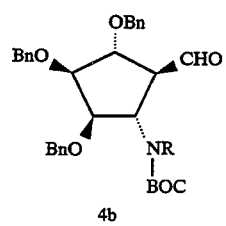
4b wherein the formyl group is in the alpha configuration can be treated with a non-nucleophilic base such as 1,8-diazabicyclo[5.4.0]undec-7-ene (DBU) at reduced temperature, preferably −78° C. to prevent elimination, which upon acidic workup results in the formula 4b aldehyde in which the formyl group is in the beta-configuration. Subsequent reduction of the aldehyde function with, for example, sodium borohydride yields the desired compound of formula 2b.

The 3H-cyclopent[c]isoxazoles of formula 3 are known in the prior art, see, for example, B. Bernet and A. Vasella, *Helv. Chim Acta* 62: 2400 (1979) or can be prepared analogously.

The compounds of formula 1 wherein R is other than a $(C_1-C_6)$alkyl or $(CH_2)_n Ar$ group can be prepared from the corresponding compound of structure 1 wherein R is hydrogen. Reductive animation with $NaBH_3CN$ and an aldehyde R'CHO wherein R' is a glycosyl moiety or protected hydroxyalkyl such as glyceraldehyde acetonide gives a compound of formula 1 or a protected derivative thereof. After any protecting groups are removed, e.g., aqueous acid if R'CHO is glyceraldehyde acetonide, the desired product of Formula 1 ($\beta,\beta$,configuration) is produced as described above.

The above recited general chemistry produces the Formula 1 compounds wherein the 3 position substituent is of the beta-configuration. The corresponding compounds of Formula 1 wherein the 3 position substituent is of the alpha-configuration are prepared analogously beginning with a structure 3 compound having the appropriate stereochemistry.

The compounds of this invention are alpha-mannosidase and alpha-fucosidase inhibitors. This can be demonstrated by the ability of the compound to inhibit Jack bean mannosidase or mannosidase II as follows:

*Mannosidase Screening Assay* (Kang, et al., Plant Physiol. 71: 551–554 (1983)). Activities of mannosidase are first screened with Jack bean enzyme using p-nitrophenyl substrate as follows using a 96-well microplate. Total Rxn mix 200λ.

1. Add compounds to be tested and dilute to 100λ with $H_2O$.
2. Add 25λ of 1M sodium acetate buffer pH 4.5 containing 10 mM $ZnCl_2$.
3. Add 25λ of enzyme (1 mμ) or approximately 0.05 μg protein.
4. Mix and incubate at R.T. for 30 min.
5. Add 50λ of 10 mM p-nitrophenyl-α-mannopyranoside in $H_2O$ to start the Rxn and incubate 37° for 30 min. Stop reaction by addition 100λ of 0.2M (2%) sodium carbonate solution (ph~12). Read absorbance at 405 nm.

*Mannosidase II Assay* (Elbein, et al., *Methods Enz. Vol.* 179, P.468). The compounds which show activity against Jack bean are checked against purified α-mannosidase II as follows with 100λ Total Rxn Volume.

1. Add compounds to be tested and dilute to 60λ with $H_2O$.
2. Add 10λ of 0.5 M MES buffer pH 6.0.
3. Add 10λ of 1% Triton X-100.
4. Add 10λ of purified enzyme and incubate 5 minutes at R.T.
5. Start the Rxn by adding 5000 CPM of GlcNAc-$Man_5$-GlcNAc substrate and incubate 37° C. for 60 min.
6. Stop reaction with 20λ of acetic acid, add 1 ml of Con A Buffer B, and determine the radioactivity released by Con A column chromatography. Using the above described procedures, the data reported in Tables 1 and 2 were obtained.

TABLE 1

$IC_{50}$ Determinations of Compounds Against α-Mannosidase II, Glycoprotein Processing Enz. (Purified)

| Compound | $IC_{50}$ μg/ml | μM |
|---|---|---|
| Swainsonine | 0.007 | 0.04 |
| 1,3β,5β,R=$CH_3$ | 0.173 | 1.0 |

TABLE 2

$IC_{50}$ Determinations of α-Mannosidase (Jack bean)

| Compound | $IC_{50}$ μg/ml |
|---|---|
| Swainsonine | 0.015 |
| 1,3β,5β,R=$CH_3$ | 0.011 |
| 1,3β,5β,R=1-methylmannosyl and mannosyl (3:1) | 0.1 |

In practicing the method of this invention, an effective amount of a compound of this invention is that amount required to elicit an immunostimulatory, antiviral or antimetastatic effect. Immunostimulatory agents are desirable in those instances where the immune system of the patient has been compromised, such as in those patients infected with HIV, the causative agent in AIDS and ARC, as well as patients undergoing bone marrow transplants, in patients having various cancers and other vital diseases. The compounds of this invention also exert a direct antiviral effect on vital diseases caused by membrane enveloped viruses such as the retroviruses, influenza viruses, cytomegaloviruses, and herpes viruses. Finally, the compounds of this invention can be used to prevent or to treat metastasis of tumors.

The specific dosage for the treatment of any specific patient in need of immunostimulant, antiviral, or antimetastatic therapy will depend upon such factors as size, type, and age of the patient as well as the severity of the disease state, all of which are factors normally familiar to and considered by the attending diagnostian treating the patient. Generally, the compounds are to be administered orally at a dose of from 0.2 to 20 mg/kg of patient body weight per day, with a dose of from 0.5 to 5 mg/kg being preferred. The compounds preferably are to be administered orally at mealtimes in single or multiple unit doses containing from 25 mg to 250 mg of the chosen compound.

In practicing the method of this invention, the active ingredient is preferably incorporated in a composition comprising a pharmaceutical carrier and from about 5 to about 90 percent by weight of a compound of the invention or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups, emulsions, dispersions and wettable and effervescent powders, and can contain suitable excipients known to be useful in the preparation of the particular type of composition desired.

The preferred route of administration is oral administration. For oral administration the formula 1 compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptable surfactant, suspending agent, or emulsifying agent.

The formula 1 compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as polyethyleneglycol 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically acceptable adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl beta-aminopropionates, and 2-alkylimidazoline quarternary ammonium salts, as well as mixtures. The parenteral compositions of this invention will typically contain from about 0.5 to about 25% by weight of the formula 1 compound in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

EXAMPLES

The following examples are presented to illustrate the present invention. However, they should not be construed as limiting it in any way.

EXAMPLE 1

Preparation of (1α,2β,3β,4α,5β)-Methyl[2,3,4-trihydroxy-5-(hydroxymethyl))cyclopentyl] amine 1a (+)-(1α,2β,3β,4α,5α)-Methyl[5-(hydroxymethyl)-2,3,4-tris(phenylmethoxy)cyclopentyl]carbamic Acid, 1,1-Dimethylethyl Ester (2a, R=CH$_3$)

A stirred mixture of 5.641 g (12.66 mmol) of the 3H-cyclopent[c]isoxazole of formula 3 (R=CH$_3$) (B. Bernet and A. Vasella, *Helv. Chim. Acta* 62: 2400 (1979)) and 2.98 g (45.6 mmol) of activated Zn dust (washed with 20% HCl, water until the filtrate was neutral, acetone, anhydrous ether) in 75 mL aqueous 85% HOAc was heated at 50°–55° C. for 1 h; additional small portions of Zn dust were added after 30 and 45 min. The mixture was partially concentrated in vacuo, then diluted with water. The aqueous solution was decanted from the residual Zn, which was subsequently washed with water, dilute aqueous KOH and EtOAc. The washings were combined and the organic layer separated. The aqueous layer was extracted twice with additional EtOAc. The combined organic extracts were washed with aqueous KOH, dilute NH$_4$OH, brine, and dried (MgSO$_4$). Concentration in vacuo gave 5.68 g of colorless oil which was dissolved in 75 mL warm (50° C.) THF containing 3.50 mL (15.2 mmol, 1.20 equivalents) of (Boc)$_2$O. An immediate evolution of gas occurred. The solution was heated at reflux for 2 h, then concentrated in vacuo. Flash chromatography eluting with 70/30 cyclohexane/EtOAc gave 6.2 g of viscous oil. Trituration with pentane gave 6.031 g (87%) of the title compound as a white solid: mp 74.5°–77° C.; IR (KBr) $\nu_{max}$ 3512, 2936, 1682, 1454, 1400, 1368, 1346, 1148, 1126, 1098, 1072, 740,698 cm$^{-1}$; $^1$H NMR (CDCl$_3$) δ7.4–7.2 (m, 15H), 4.72–4.42 (m, 7H, including 4.52 (d, J=12 Hz) and 4.44 (d, J=12 Hz)), 4.32–4.17 (m, 1H), 4.01 (d, 0.5H, J=2 Hz), 3.99 (d, 0.5H, J=2 Hz), 3.96–3.86 (m, 1H), 3.63–3.54 (m, 2H), 2.8 (m, 1H), 2.79 and 2.74 (2s, 3H), 2.63 (m, 0.5H), 2.17 (m, 0.5H),1.47 (s, 9H); mass spectrum, m/z 548 (M$^+$+1), 490, 476, 474, 449, 448 (100);[α]$_D^{25}$+56.3° (c 0.27, CHCl$_3$). Anal. Calcd for C$_{33}$H$_{41}$NO$_6$: C, 72.37; H, 7.55; N, 2.56. Found: C, 72.22; H, 7.58; N, 2.52.

1b (1α,2α,3α,4β,5β)-[2-Formyl-3,4,5-tris(phenylmethoxy)cyclopentyl]methylcarbamic Acid, 1,1-dimethylethyl Ester (4a, R=CH$_3$)

To a stirred suspension of 2.603 g (6.16 mmol) of the Dess-Martin periodinane reagent in 70 mL CH$_2$Cl$_2$ was added a solution of 1.83 g (3.34 mmol) of the product of 1a in 20 mL CH$_2$Cl$_2$ (+2 ×5 ml CH$_2$Cl$_2$ rinses). The mixture was stirred for 1.25 h, diluted with ether, and then poured into water containing 13 g (130 mmol) of KHCO$_3$ and 6 g (38 mmol) of Na$_2$S$_2$O$_3$.5H$_2$O. When both layers became clear, the organic layer was separated, washed with brine, and dried (MgSO$_4$). Concentration in vacuo gave 1.85 g (100%) of the title compound as a colorless oil: $^1$H NMR (CDCl$_3$) δ9.68 (bs, 1H), 7.4–7.1 (m, 15H), 4.75–4.35 (m, 8H), 4.19–3.86 (m, 2H), 3.30 (bs, 1H), 2.78 and 2.72 (2s, 3H), 1.45 (s, 9H).

1c
(1α,2β,3α,4β,5β)-[2-Formyl-3,4,5-tris(phenylmethoxy) cyclopentyl]methylcarbamic Acid, 1,1-Dimethylethyl Ester (4b, R=CH$_3$)

To a stirred solution of 1.85 g (3.34 mmol) of the product of 1 b in 45 mL CH$_2$Cl$_2$ at −78° C. under nitrogen was added 0.27 mL (1.8 mmol) of 1,8-diazabicyclo[5.4.0]undec-7-ene (DBU) dropwise via syringe. After 37 min the solution was quenched at −78° C. by addition of 0.20 mL (3.5 mmol) of HOAc. The solution was poured into ether, washed with water, dilute KHCO$_3$, and brine, and dried (MgSO$_4$). Concentration in vacuo gave 1.87 g (100%, trace of CH$_2$Cl$_2$ and ether present) of the title compound as a colorless oil: $^1$H NMR (CDCl$_3$) δ9.69 (s, 1H), 7.4–7.23 (m, 15H), 4.86 (t, 1H, J=8.4 Hz), 4.6–4.4 (m, 6H), 4.15–4.05 (m, 2H), 3.87 (bs, 1H), 2.74 (bs, 4H), 1.45 (s, 9H).

1d
(+)-(1α,2β,3β,4α,5β)-Methyl[5(hydroxymethyl)-2,3,4-tris(phenylmethoxy)cyclopentyl]carbamic Acid, 1,1-dimethylethyl Ester (2b, R=CH$_3$)

To a stirred solution of 202 mg (0.370 mmol) of the compound of 1c in 10 mL absolute EtOH was added 16 mg (0.42 mmol) of NaBH$_4$. After 15 min the reaction mixture was quenched by the addition of HOAc, then neutralized with NaHCO$_3$. The mixture was partially concentrated in vacuo, diluted with aqueous NaOH, and extracted with several portions of ether. The combined extracts were washed with brine, dried (MgSO$_4$), and concentrated in vacuo to give 184 mg (91%) of the title compound as a near colorless oil. Flash chromatography eluting with 22.5% EtOAc in cyclohexane gave the title compound as a colorless oil: IR (neat) ν$_{max}$ 3458, 2976, 2930, 2870, 1692, 1668, 1454, 1392, 1366, 1152, 1090, 1074, 1028, 736, 698 cm$^{-1}$; $^1$H NMR (CDCl$_3$) δ7.38–7.25 (m, 15H), 4.65–4.37 (m, 7H), 3.98 (dd, 1H, J=8.9, 5 Hz), 3.84 (dd, 1H, J=5, 2.5 Hz), 3.81–3.54 (m, 4H), 2.70 and 2.64 (2 s in ~1:2.5 ratio, 3H), 1.98 and 1.88 (2 bs in 3:8 ratio, 1H), 1.48 (s, 9H); mass spectrum, m/z 548 (M$^+$+1), 493, 492 (100), 476, 449, 448, 384, 91; [α]$_D^{25}$+44.8° (c 1.02, CHCl$_3$). Anal. Calcd for C$_{33}$H$_{41}$NO$_6$:C, 72.37; H, 7.55; N, 2.56. Found: C, 72.42; H, 7.70; N, 2.35.

1e
(+)-(1α,2β,3β,4α,5β)-Methyl[2,3,4-trihydroxy-5-(hydroxymethyl)-cyclopentyl]carbamic Acid, 1,1-Dimethylethyl Ester Hydrogenation of a solution of 2.723 g (4.97 mmol) of the product of 1d in 50 mL CH$_3$OH containing 0.30 g Pd black as catalyst in a Parr hydrogenation apparatus for 4 days gave 1.51 g of a pale yellow oil. Flash chromatography eluting with 12% CH$_3$OH in EtOAc gave 1.294 g (94%) of the title compound as white crystals: mp 81°–83° C.; IR (KBr) ν$_{max}$ 3420, 2974, 2930, 1690, 1666, 1368, 1158, 1046, 886 cm$^{-1}$; $^1$H NMR (CDCl$_3$) δ5.22 (bd, 2H, J=5.6 Hz), 4.64 (bs, 1H), 4.58 (bs, 1H), 4.15 (bs, 2H), 3.94 (bs, 1H), 3.73 (bs, 1H), 3.54 (bs, 1H), 2.81 (s, 3H), 1.78 (bs, 1H), 1.44 (s, 9H); FABMS(-glycerol), m/z 278 (M$^+$+1, 100), 222 (100), 204, 178;[α]$_D^{25}$+30.8° (c 1.06, CHCl$_3$). Anal. Calcd for C$_{12}$H$_{23}$NO$_6$: C, 51.97; H, 8.36; N, 5.05. Found: C, 52.03; H, 8.59; N, 4.83.

1f
(1α,2β,3β,4α,5β)-Methyl[2,3,4-trihydroxy-5-(hydroxymethyl) cyclopentyl]amine (1, R=CH$_3$, 3β,5β-configuration)

Gaseous HCl was bubbled through an ice-cold solution of 1.255 g (4.53 mmol) of the product of 1e in 125 mL ether/CH$_3$OH for 20 min. The solution was allowed to warm to 25° C. overnight, then concentrated in vacuo. The residue was chromatographed eluting with 3:1:2 CH$_3$OH:conc NH$_4$OH:CH$_2$Cl$_2$. The amino alcohol was dissolved in EtOH and the solvent removed in vacuo. The material was redissolved in EtOH and filtered through filter aid. Concentration in vacuo gave a pale straw-colored glass which was dissolved in water and treated with activated charcoal. Filtration through filter aid and concentration in vacuo gave 0.686 g (85%) of 7 as a colorless glass which slowly crystallized on standing: $^1$H NMR (D$_2$O) δ3.86–3.59 (m, 5H), 2.61 (dd, 1H, J=7.3, 2.9 Hz), 2.31 (s, 3H), 1.55 (m, 1H); $^{13}$C NMR (D$_2$O) δ79.34, 78.16, 75.94, 67.98, 64.28, 52.10, 35.92.

Preparation of (1α,2β,3β,4α,5β)-[2,3,4-trihydroxy-5-(hydroxymethyl)cyclopentyl]amine (1, R=H,3β,5β-configuration)

EXAMPLE 2

Preparation of (1α,2β,3β,4α,5β)-[2,3,4-trihydroxy-5-(hydroxymethyl)cyclopentyl]amine (1, R=H,3),5)-configuration.

2a 3H-Cyclopent[c]isoxazole (3, R=CH$_2$Ph)

The title compound was prepared in 71% yield using a procedure analogous to the reported method (B. Bernet and A. Vasella, Helv. Chim. Acta 62: 2400 (1979)). Recrystallization from hexane/cyclohexane gave white crystals: mp 68.5°–70.5° C.; IR (KBr)ν$_{max}$ 3436, 2874, 1454, 1138, 1114, 1088, 1026, 1014, 752, 730, 698 cm$^{-1}$; $^1$H NMR (CDCl$_3$) δ7.37-7.24 (m,18H), 7.18–7.14 (m,2H), 4.72 (d,1H,J=12.0 Hz), 4.57 (d,1H,J=12.0 Hz), 4.54 (d,1H,J=12.0 Hz), 4.52 (d,1H,J=12.0 Hz), 4.36 (d,1H,J=12.2 Hz). 4.26 (d,1H,J=12.2 Hz), 4.24 (t,1H,J=8 Hz), 4.19 (dd,1H,J=9.0, 3.5 Hz), 4.02 (d,1H,J=12.5 Hz), 3.93 (dd,1H,J=8.8, 4.8 Hz), 3.89 (dd,1H,J=9.0, 7.9 Hz), 3.71 (d,1H,J=12.5 Hz), 3.67 (dd,1H, J=4.8, 1.1 Hz), 3.47 (bd,1H,J=8.3 Hz), 3.26 (qd,1H,J=8.1, 3.5 Hz); $^{13}$C NMR (CDCl$_3$) 138.60, 138.54, 138.07, 136.86, 129.25, 128.50, 128.34, 128.27, 128.24, 127.96, 127.62, 127.55, 127.52, 127.42, 82.53, 81.35, 79.40, 72.62, 72.37, 71.61, 70.28, 65.54, 60.53, 45.60; mass spectrum, m/z 550 (M$^+$+29), 523, 522 (M$^+$+1, 100), 444, 432, 91; [α]$_D^{20}$−69.0° (c 1.05, CHCl$_3$). Anal. Calcd for C$_{34}$H$_{35}$NO$_4$: C, 78.28H, 6.76; N, 2.69. Found: C, 78.41H, 6.83; N, 2.62.

2b
(+)-(1α,2β,3β,4α,5α)-Phenylmethyl[5-(hydroxymethyl)-2,3,4-tris(pheneylmethoxy)cyclopentyl]carbamic Acid, 1,1-dimethylethyl Ester (2a,R=CH$_2$Ph)

Using a similar procedure, flash chromatography eluting with 2:1 cyclohexane/EtOAc gave the title compound in 89.5% yield as a clear glass: IR (CHCl$_3$)

$\nu_{max}$ 3460, 2930, 1690, 1454, 1366, 1168, 1122, 736, 698 cm$^{-1}$; $^1$H NMR (CDCl$_3$) $\delta$7.43–7.05 (m,20H), 4.80–4.45 (m,7H), 4.28–3.85 (m,5H), 3.65–3.31 (m,4H), 2.75–2.64 (m,1H), 1.43 and 1.24 (2s in 1:2 ratio, 9H); mass (51.9° (c 1.07, CHCl$_3$). Anal. Calcd for C$_{39}$H$_{45}$NO$_6$: C, spectrum, m/z 624 (M$^+$+1), 552, 525, 524 (100), 91; [$\alpha$]$_D^{20}$+75.09; H,7.27; N, 2.25. Found: C, 75.42H, 7.36; N, 2.20.

2c
(1$\alpha$,2$\alpha$,3$\alpha$,4$\beta$,5$\beta$)-[2-Formyl-3,4,5-tris(phenylmethoxy)cyclopentyl]phenylmethylcarbamic Acid,1,1-Dimethylethyl Ester (4a, R=CH$_2$PH)

Using a similar procedure, the crude title compound was obtained as a pale yellow viscous oil: $^1$H NMR (CDCl$_3$) $\delta$9.77 and 9.66 (2 bs in 3:1 ratio, 1H), 7.43–7.18 (m,18H), 7.16–7.10 (m,2H), 4.8–3.75 (m,12H), 3.24–3.15 (m,1H), 1.42 (s,9H).

2d
(+)-(1$\alpha$,2$\beta$,3$\beta$,4$\alpha$,5$\beta$)-Phenylmethyl[5-hydroxymethyl)-2,3,4-tris(phenylmethoxy)cyclopentyl]carbamic Acid, 1,1-Dimethylethyl Ester (2b, R=CH$_2$Ph)

Using similar procedures, 4a (R=CH$_2$Ph) was partially epimerized to a mixture of 4a and 4b (R=CH$_2$Ph) and the mixture was reduced with NaBH$_4$ to give after flash chromatography on silica gel eluting with 20% EtOAc in cyclohexane 50% of 2b (R=CH$_2$Ph) and 22% of the more polar 2a (R=CH$_2$Ph). The title compound was obtained as a clear viscous syrup: IR (CHCl$_3$ film) $\nu_{max}$ 3458, 2930, 1690, 1454, 1366, 1166, 1128, 1090, 1074, 752, 736, 698 cm$-1$; $^1$H NMR (CDCl$_3$) $\delta$7.38–7.15 (m,20H), 4.80 (t,1H,J=5 Hz), 4.59–3.80 (m,12H), 3.60–3.52 (m,1H), 3.4–3.3 (m,1H obscured by H$_2$O peak), 2.04–1.93 (m,1H), 1.39 and 1.26 (2s in 1:2 ratio, 9H);mass spectrum, m/z 624 (M$^+$+1), 568, 524, 460, 93, 92, 91(100); [$\alpha$]$_D^{20}$+57.1° (c 1.05, CHCl$_3$). Anal. Calcd for C$_{39}$H$_{45}$NO$_6$: C, 75.09; H, 7.27; N, 2.25. Found: C, 75.25; H, 7.30; N, 2.32.

2e
(1$\alpha$,2$\beta$,3$\beta$,4$\alpha$,5$\beta$)-Phenylmethyl[2,3,4-trihydroxy-5-(hydroxymethyl)cyclopentyl]amine (1,R=CH$_2$Ph,3$\beta$,5$\beta$-configuration) and

2f
(1$\alpha$,2$\beta$,3$\beta$,4$\alpha$,5$\beta$)-[2,3,4-trihydroxy-5-(hydroxymethyl)cyclopentyl]amine (1,R=H, 3$\beta$,5$\beta$-configuration)

A solution of 1.31 g (2.1 mmol) of 2b (R=CH$_2$Ph) in 40 ml HOAc containing 349 mg Pd black was hydrogenated in a Parr shaker for 4 days. The isolated crude material was dissolved in 12 ml 3:1 EtOH/cyclohexene and 105 mg PdO was added. The stirred mixture was heated at reflux under nitrogen for 2 days. The crude mixture was resubjected to catalytic hydrogenation (Parr) for 4 more days using 20 ml HOAc as solvent and 185 mg Pd black and finally for 3 days using 20 ml EtOH containing 1 ml conc HCl as solvent and 165 mg Pd black. Chromatography of the crude mixture on silica gel eluting with 3:1:2 CH$_3$OH: conc NH$_4$OH: CH$_2$Cl$_2$ gave 234 mg of partially purified 1 (R=CH$_2$Ph, $\beta$, $\beta$-configuration) [after trituration with CH$_3$OH to remove some insoluble material] and 168 mg of the partially purified more polar 1 (R=H,$\beta$,$\beta$-configuration). For 1 (R=CH$_2$Ph, $\beta$,$\beta$-configuration): $^1$H NMR (D$_2$O, no DSS) $\delta$7.48–7.41 (m,5H), 4.78 (HOD), 4.35 (t,1H,J=5.8 Hz), 4.34 (d,1H,J=12.9 Hz), 4.25 (d,1H,J=12.9 Hz), 3.95 (t,1H,J=5.9 Hz), 3.81 (t,1H,J=6.4 Hz), 3.76 (dd,1H,J=11.5, 5.4 Hz), 3.64 (dd,1H,J=11.5, 6.4 Hz), 3.32 (dd,1H,J=8.0, 5.2 Hz), 2.02 (m,1H). For 1 (R=H, $\beta$,$\beta$-configuration): $^1$H NMR (D$_2$O, no DSS) $\delta$4.80 (HOD), 3.9–3.63 (m,5H), 3.05–2.97 (m,1H), 1.71–1.6 (m,1H).

EXAMPLE 3

Preparation of (1$\alpha$,2$\beta$,3$\beta$,4$\alpha$,5$\beta$)-[2,3,4-trihydroxy-5-(hydroxymethyl)cyclopentyl]-1',3'-dihydroxyprop-2-ylamine (1, R=1,3-dihydroxyprop-2-yl; 3$\beta$,5$\beta$-configuration)

3a Preparation of (1$\alpha$,2$\beta$,3$\beta$,4$\alpha$,5$\beta$)-[2,3,4-tris(phenylmethoxy)-5-(hydroxymethyl)cyclopentyl-(1',3'-dihydroxyprop-2'-yl)amine A mixture of (1$\alpha$,2$\beta$,3$\beta$,4$\alpha$,5$\beta$)-[2,3,4-tris(phenylmethoxyl-5-(hydroxymethyl)cyclopentylamine, (1.15 g, 2.65 mmol), 2,5-dihydroxy-(2,5-dihydroxymethyl)dioxane (497 mg, 2.76 mmol), and NaBH$_3$CN (202 mg, 3.21 mmol) in 17 ml CH$_3$OH was stirred at room temperature. After 17 hours, an additional 42 mg (0.23 mmol) of 2,5-dihydroxy-2,5-(dihydroxymethyl)dioxane was added. After 4 more days the reaction mixture was treated with aqueous potassium hydroxide/ethyl acetate, the extracts washed with brine, dried over MgSO$_4$ and concentrated in vacuo. This gave 1.42 g of the product as an amber oil. Flash chromatography on silica gel with 10% CH$_3$OH/1% NH$_4$OH/CH$_2$Cl$_2$, 368 mg (27%); m/z 508 (M+H$^+$, 100).

3b Preparation of (1$\alpha$,2$\beta$,3$\beta$,4$\alpha$,5$\beta$)-[2,3,4-trihydroxy-5-(hydroxymethyl)cyclopentyl]-1',3'-(dihydroxyprop-2'-yl)amine A mixture of the product of Example 3a, (366 mg, 0.721 mmol) and 50 mg Pd black in 10 ml acetic acid was shaken in a Parr hydrogenation apparatus f or 8 days. The catalyst was then removed (HOAc rinse) and the filtrate concentrated in vacuo. The product was then isolated by ion exchange chromatography, run [AG 50 W-X8 (Bio-Rad)] eluting with 0.1N NH$_4$OH followed by ion exchange chromatography run eluting with first 0.1N HCl, then 0.5N HCl, which after lyophilization from H$_2$O gave 125 mg of a colorless glass.

EXAMPLE 4

Preparation of (1$\alpha$,2$\beta$,3$\beta$,4$\alpha$,5$\beta$)-6-deoxy-6-mannosyl[2,3,4-trihydroxy-5-(hydroxymethyl)cyclopentyl]amine and (1$\alpha$,2$\beta$,3$\beta$,4$\alpha$,5$\beta$)-6-deoxy-1-O-methyl-6-mannosyl[2,3,4-trihydroxy-5-(hydroxymethyl)cyclopentyl]amine. (1, R=6-deoxy-6-mannosyl and R=6-deoxy-1-O-methyl-6-mannosyl)

4a A mixture of (1,2,3,4,5)-2,3,4-tris(phenylmethoxy)-5-(hydroxymethyl)cyclopentylamine, 228 mg (0.526 mmol) and 6-bromo-6-deoxy-1-O-methyl-2,3,4-tris(phenylmethoxy)mannose, 312 mg (0.592 mmol) and 0.77 g (7.7 mmol) KHCO$_3$ in 6 ml toluene heated at reflux with stirring under N$_2$ for 6 days. Workup with aqueous KOH/EtOAc, brine wash and drying over MgSO$_4$ gave the crude material which was purified by flash chromatography on silica gel eluting with 70/30 EtOAc/cyclohexane to give 147 mg (32%) pale yellow oil.

4b A mixture of product from 4a (386 mg, 0.439 mmol) and 65 mg Pd black in 10 ml of acetic acid was hydrogenated in a Parr shaker for 9 days. The product was concentrated in vacuo and purified by ion exchange chromatography [AG 50W-X8 (Bio-Rad)] using first 0.1N then 0.5N HCl gives 142 mg of a pale yellow (straw) colored foam/glass. NMR and high res. m/z show ~1:3 mix of the title compounds.

Cl$_{12}$H$_{23}$NO$_9$.HCl: m/z (M+1)+326 and

C$_{13}$H$_{25}$NO$_9$.HCl: m/z (M+1)+340.

We claim:

1. A compound of the formula

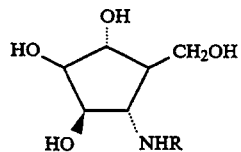

wherein R is a (C$_1$-C$_6$)alkyl optionally substituted with one or two hydroxy groups, a glycosyl group, a group of the formula —(CH$_2$)$_n$—Ar, wherein n is an integer of from 1 to 4 and Ar is a phenyl optionally substituted with one or two groups selected from (C$_1$-C$_4$)alkyl, (C$_1$-C$_4$)alkoxy, fluoro, chloro, bromo, iodo, amino, mono(C$_1$-C$_4$)alkylamino or di(C$_1$-C$_4$)alkylamino, or a pharmaceutically acceptable salt thereof.

2. A compound of claim 1 wherein R is a methyl, ethyl, 2,3-dihydroxypropyl, or a mannosyl group.

3. A compound of claim 1 wherein the hydroxymethyl group is of the beta-configuration.

4. A compound of claim 2 wherein the hydroxymethyl group is of the beta-configuration.

* * * * *